United States Patent
Chuinard

(10) Patent No.: US 11,523,677 B1
(45) Date of Patent: Dec. 13, 2022

(54) SURGICAL BRUSH CARTRIDGE FOR SONIC SKIN CLEANER

(71) Applicant: Christopher R. Chuinard, Traverse City, MI (US)

(72) Inventor: Christopher R. Chuinard, Traverse City, MI (US)

(*) Notice: Subject to any disclaimer, the term of this patent is extended or adjusted under 35 U.S.C. 154(b) by 0 days.

(21) Appl. No.: 16/386,827

(22) Filed: Apr. 17, 2019

Related U.S. Application Data

(60) Provisional application No. 62/659,323, filed on Apr. 18, 2018.

(51) Int. Cl.
| | |
|---|---|
| *A46B 13/02* | (2006.01) |
| *A46B 11/00* | (2006.01) |
| *A46B 5/00* | (2006.01) |
| *A61B 90/80* | (2016.01) |
| *A47K 7/03* | (2006.01) |

(52) U.S. Cl.
CPC .......... *A46B 13/023* (2013.01); *A46B 5/0095* (2013.01); *A46B 11/001* (2013.01); *A47K 7/03* (2013.01); *A61B 90/80* (2016.02)

(58) Field of Classification Search
CPC ... A46B 11/0003; A46B 13/023; A46B 13/04; A46B 5/0095; A46B 17/04; A61M 35/003; A61M 35/006; A61C 17/222; A61C 2202/00; A61B 2050/0065
See application file for complete search history.

(56) References Cited

U.S. PATENT DOCUMENTS

| | | | |
|---|---|---|---|
| 2,970,073 A | 1/1961 | Prange | |
| 3,165,776 A * | 1/1965 | Tuseth | A46B 11/0003 401/132 |
| 3,396,419 A | 8/1968 | Richter et al. | |
| 4,148,318 A | 4/1979 | Meyer | |
| 4,198,171 A * | 4/1980 | Lampka | A46B 7/04 401/269 |

(Continued)

FOREIGN PATENT DOCUMENTS

| | | |
|---|---|---|
| WO | 9955280 A2 | 11/1999 |
| WO | WO-2007117254 A1 * 10/2007 | ......... A46B 15/0091 |

OTHER PUBLICATIONS

Clarisonic, Clarisonic Men's Facial Cleansing Brush Head Replacement, Amazon.com advertisement, Jun. 29, 2017 (earliest review), 9 pages, www.amazon.com, U.S.

(Continued)

*Primary Examiner* — David P Angwin
*Assistant Examiner* — Bradley S Oliver
(74) *Attorney, Agent, or Firm* — Mitchell Intellectual Property Law, PLLC

(57) ABSTRACT

A disposable brush head cartridge for a sonic or ultrasonic skin cleaning brush, specially adapted for use in surgical skin prep. The disposable brush head cartridge has a base configured to be removably attached to a sonic motor drive handle. The disposable brush head cartridge further comprises an upper bristle head sealed with respect to the base by a surrounding disposable cover spaced from the bristles. The cover defines a reservoir of pre-surgical skin cleaning fluid, in a first form soaking or pre-moistening the brush bristles until the cover is removed, and in a second form stored in a separate fluid-tight compartment in the cover and combined with the brush bristles after the cover is removed.

3 Claims, 7 Drawing Sheets

(56) References Cited

U.S. PATENT DOCUMENTS

| | | | | |
|---|---|---|---|---|
| 6,062,233 | A | * | 5/2000 | Williams .............. A45D 44/18 |
| | | | | 132/308 |
| 6,135,274 | A | * | 10/2000 | James ................ A46B 11/0003 |
| | | | | 206/362.2 |
| 6,569,170 | B1 | | 5/2003 | Kellogg |
| 8,069,523 | B2 | | 12/2011 | Vaillancourt et al. |
| 2008/0087568 | A1 | * | 4/2008 | Jabri ................. A46B 15/0091 |
| | | | | 206/570 |

OTHER PUBLICATIONS

BD, Surgical Scrub Brush, Pack of 30, Amazon.com advertisement, Apr. 21, 2014 (earliest review), 6 pages, www.amazon.com, U.S.
3M, DuraPrep Surgical Solutions "prep stick", product photos, Feb. 2018, 2 pages, photographs taken by applicant, U.S.

* cited by examiner

SURGICAL BRUSH CARTRIDGE FOR SONIC SKIN CLEANER

RELATED APPLICATIONS/PRIORITY BENEFIT CLAIM

This application claims the benefit of U.S. Provisional Application No. 62/659,323, filed Apr. 18, 2018 by the same inventor (Chuinard), the entirety of which provisional application is hereby incorporated by reference.

FIELD

The subject matter of the present application is in the field of sonic skin cleaning brushes and surgical skin cleaning.

BACKGROUND

Sonic brushes are known for cosmetically cleaning skin. The bristles in such brushes do not rotate or reciprocate, but oscillate minutely at sonic or ultrasonic frequencies to clean skin more effectively than manual or motorized brushes.

One patent example is shown in U.S. Pat. No. 6,569,170 to Kellogg, which shows a sonic battery-powered brush with a bristle head perpendicular to the handle. The brush head transmits ultrasonic vibration to the skin via the bristles, and works in conjunction with skin cleaning soap, detergent, or solvent applied directly to the skin or added to the bristles.

A commercial example of a sonic skin cleaning brush is the Clarisonic® facial cleansing brush having a brush head coaxial with the handle. The brush head is removably attached to a barrel-like body using a bayonet style fitting.

Sponges are known for preparing a patient's skin for surgery by removing oil, fat, and dirt, in part to enhance the efficacy of antiseptics/disinfectants subsequently applied to the skin. Patented examples include U.S. Pat. No. 3,396,419 to Richter et al, in which a surgical scrub sponge with different pore zones is impregnated with a liquid detergent composition containing antibacterial agents; and, U.S. Pat. No. 8,069,523 to Vaillancourt et al, in which a "brush" made from a block of foam material receives a cleaning or disinfectant solution and is then sealed with a thin barrier layer about its periphery and bottom and covered with a removable foil lid or cover over the top.

BRIEF SUMMARY

The present invention is a sonic or ultrasonic (hereafter "sonic") skin cleaning brush specially adapted for use in surgical skin prep. The brush comprises a handle with a power source and a sonic motor, and a disposable brush cartridge with a base configured to be removably attached to the handle. The disposable brush cartridge further comprises an upper bristle head sealed with respect to the base.

In a first form, the sealed bristle head comprises a reservoir of pre-surgical skin cleaning fluid around the bristles to keep the bristles in a pre-soaked or pre-moistened condition.

The pre-surgical skin cleaning fluid preferably comprises a solution of antiseptic and detergent to simultaneously remove oil and fat and sterilize the skin at the surgical site. "Antiseptic" and "detergent" should be understood broadly herein, to include any known antibacterial/antiviral agents and any known skin cleaning agents. Preferred components of the pre-surgical skin cleaning fluid include benzoyl peroxide, salicylic acid, and/or azelaic acid, singly or in various combinations.

In a further variation on the first form, the sealed bristle head includes a removable, disposable fluid-tight cover configured to be removed from the disposable brush cartridge after the disposable brush cartridge has been attached to the handle, reducing the possibility of contaminating the bristles.

In a second form, the sealed bristle head comprises two compartments, with the brush bristles sealed in a first compartment, and the pre-surgical cleaning fluid contained in a second compartment and combined with the brush bristles by pouring it over the brush bristles or dipping the brush bristles into the fluid after the cover is removed. The fluid may also be contained in the second compartment in its own fluid-tight container, such as a small pouch, rather than as a free fluid.

In a third form, the sealed bristle head comprises a single sealed compartment around the bristle head until the cover is removed, and the pre-surgical cleaning fluid is combined with the brush cartridge in its own sealed pouch or similar small container inside the sealed compartment, the pouch being opened and applied to the brush bristles after the cover is removed.

These and other features and advantages of the invention will become apparent from the detailed description below, in light of the accompanying drawings.

DETAILED DESCRIPTION

Figure 1:
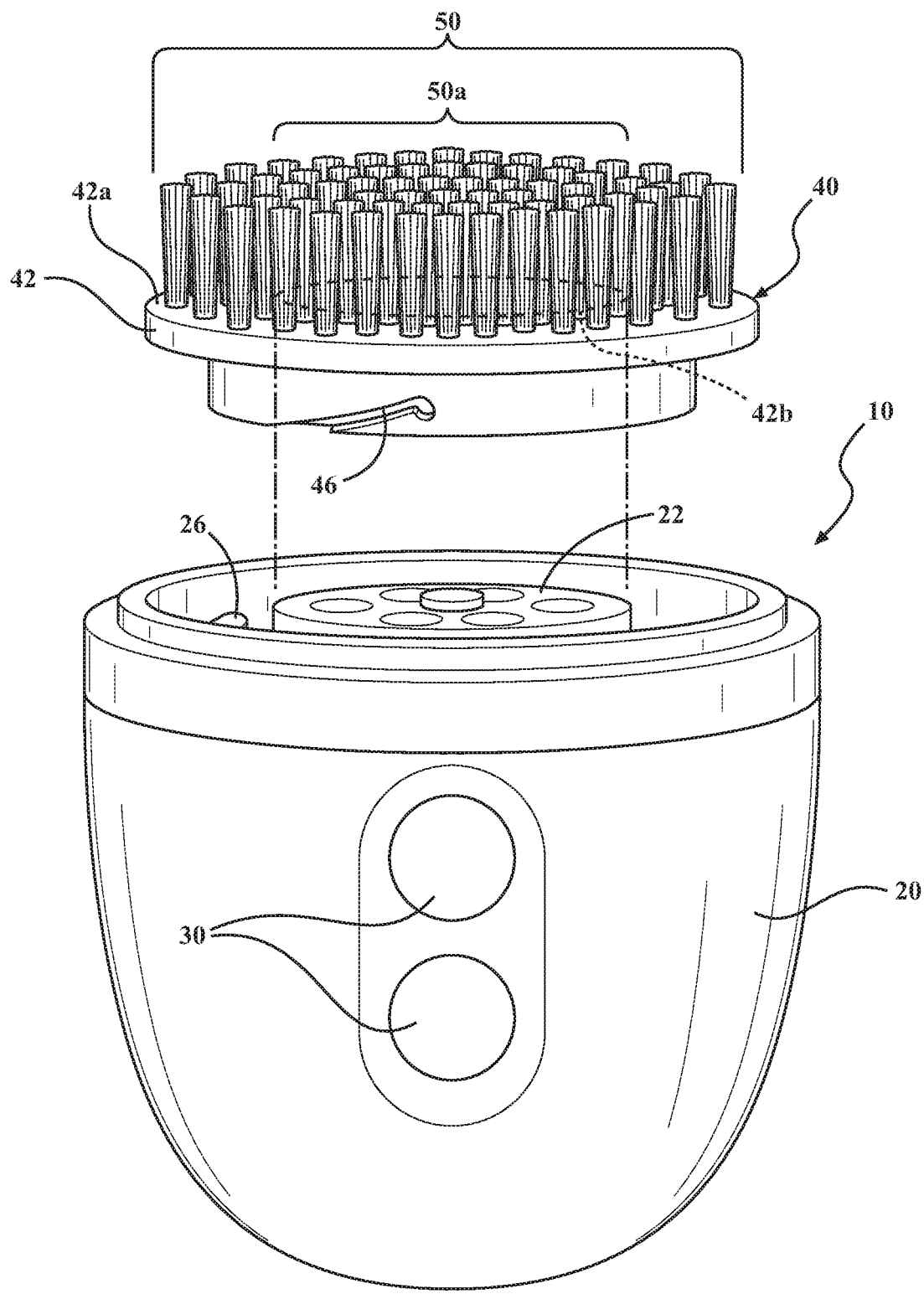
FIG. 1 is an exploded perspective view of a prior art sonic skin cleaning brush with a removable bristle head.

Referring first to FIG. 1, a prior art cosmetic sonic skin cleaning brush 10 is illustrated, for example representing the commercially available Clarisonic® facial cleansing brush. Brush 10 includes a handle 20 with control and/or power buttons 30 operating a sonic vibrating motor and its battery power source (not shown) located in handle 20. A removable, re-usable sonic brush head 40 has a base 42 configured to be removably attached to a sonic drive member or coupling 22 located at the top or end of handle 20, the sonic member being vibrated sonically or ultrasonically by the motor in the handle. Base 42 can be configured for a removable connection to the handle 20 and member 22 with any known type of non-permanent connection, for example with mating twist-lock bayonet features such as slots 46 and lugs 26 of known type.

Brush head 40 includes an array of bristles 50 on the upper face 42a of base 42. Bristles 50 are of a known type designed to efficiently transmit sonic energy received by the base to the skin of a person using the brush. Specific to the Clarisonic® facial cleansing brush pictured represented in FIG. 1, and generally known to those skilled in the art, an inner portion 42b of base 42 supporting an inner region of bristles 50a may be movably coupled to base 42 and sonically coupled to sonic drive member 22 so that inner portion 42b and inner bristle region 50a are vibrated sonically or ultrasonically independently of the outer base member 42 (and outer region 50 of the bristles) which may be locked to the outer wall of handle 20 by lugs 26.

While sonic brush 10 is shown as an in-line model, with the axis of handle 20 in line with the axis of brush head 40, such brushes are also available with brush heads offset from the handle axis.

Referring now to FIGS. 2-5, a disposable brush head cartridge 100 is shown in exemplary form in order to teach how to make and use the claimed invention.

Brush head cartridge 100 is shown operatively connected to a handle 20, handle 20 being functionally similar or identical to handle 20 in FIG. 1. Handle 20 may have an internal sonic motor 20a powered by a battery or external electrical current supply 20b, motor 20a having a sonic coupling 21 to sonic drive member 22 on the upper end of the handle, or equivalent known structures to achieve sonic/ultrasonic vibration of some or all of the bristles in brush head cartridge 100 in known manner. Brush head cartridge 100 is shown being coupled to an in-line type sonic brush handle 20, but could also be coupled to a sonic brush handle of known type with an offset or other type of known sonic brush handle using known connecting structures.

Brush head cartridge 100 includes a base 102 configured to be connected to the sonic drive member 22 in the same or a similar manner as base 40 in FIG. 1, the particular manner of removable attachment not being critical to the present invention and within the understanding of those skilled in the art. Base 102 has an upper face 102a supporting an array of sonic skin cleaning bristles 104 of known type, for example in a manner similar or identical to the base and bristle structure 42, 50 shown in the example of FIG. 1, such that connection to handle 20 sonically (or ultrasonically) vibrates some or all of base 102 and bristles 104 in the same or similar known manner. In the illustrated example the upper face 102a has a stepped configuration with a smaller diameter raised bristle-supporting surface 102a' best seen in FIG. 3, but upper face 102a could alternately be a continuous flat surface similar to upper face 42a in FIG. 1. The invention is not limited to use with the Clarisonic type brush head schematically shown in FIG. 1, and may be used with brush heads that do not have independently vibrating sections such as 42b, 50a but rather have solid bases and unitary bristle arrays which are vibrated in their entirety relative to handle 20. Brush head cartridge 100 in FIGS. 2 through 6 may be considered to schematically represent either type.

According to the present invention, brush head cartridge 100 further includes a thin-walled, substantially rigid, fluid-tight plastic cover 110 surrounding bristles 104 and sealed in fluid-tight manner to base 102, for example sealed by heat or sonic welding or molding to upper face 102a of the base around the perimeter of the bristle array, or sealed around the perimeter of the outer sidewall of base 102 below the upper face 102a. In the illustrated example, the type of plastic used for 110 may be any known polymer material such as HDPE or polycarbonate material, and may be opaque, translucent, or transparent. Base 102 is likewise preferably made of a known plastic material suitable for receiving the lower perimeter edge 110a of cover 110 in a sealed connection.

Figure 3:
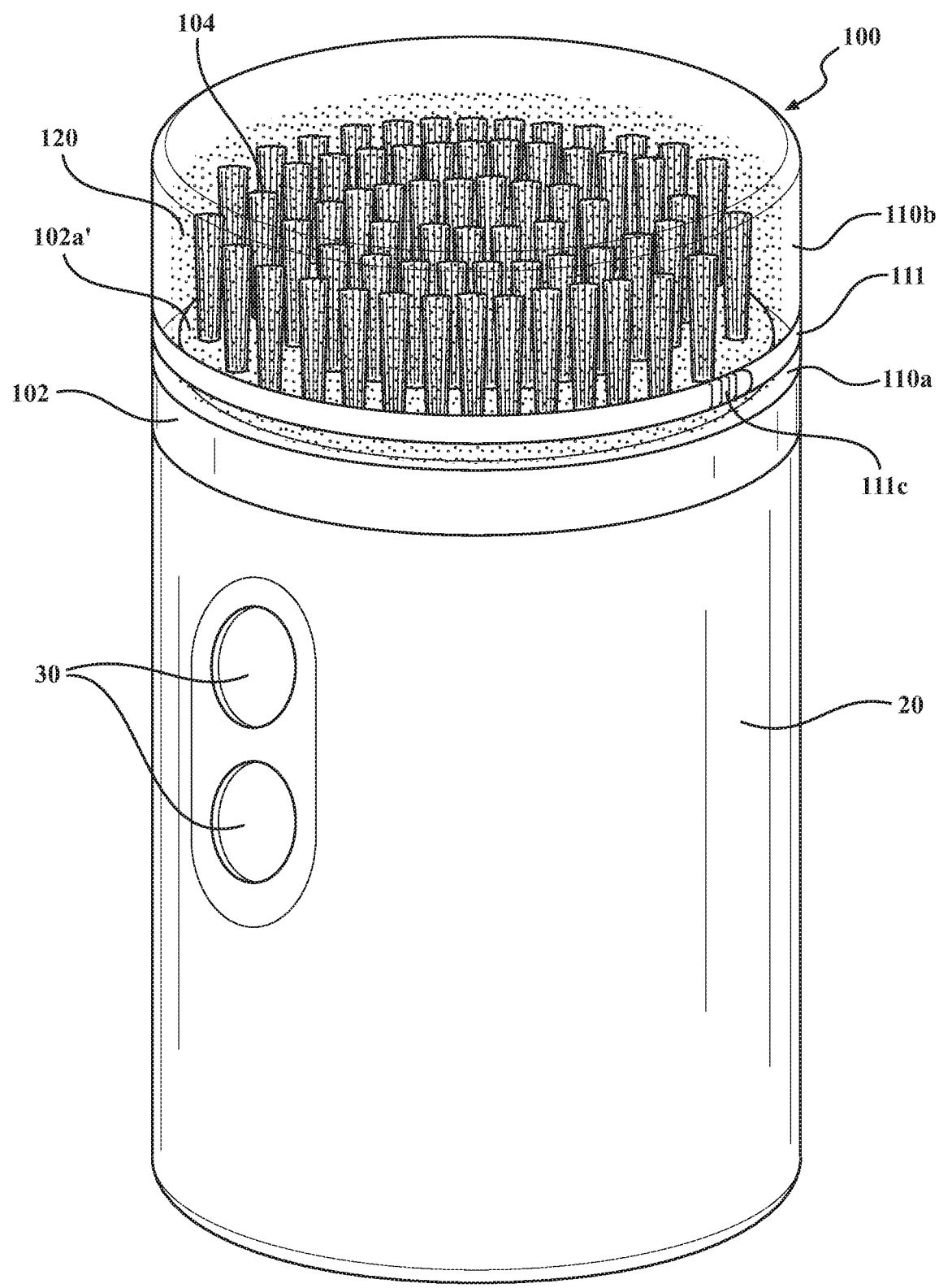
FIG. 3 is a perspective view of the assembled sonic brush handle and brush cartridge of FIG. 2.
Figure 4:
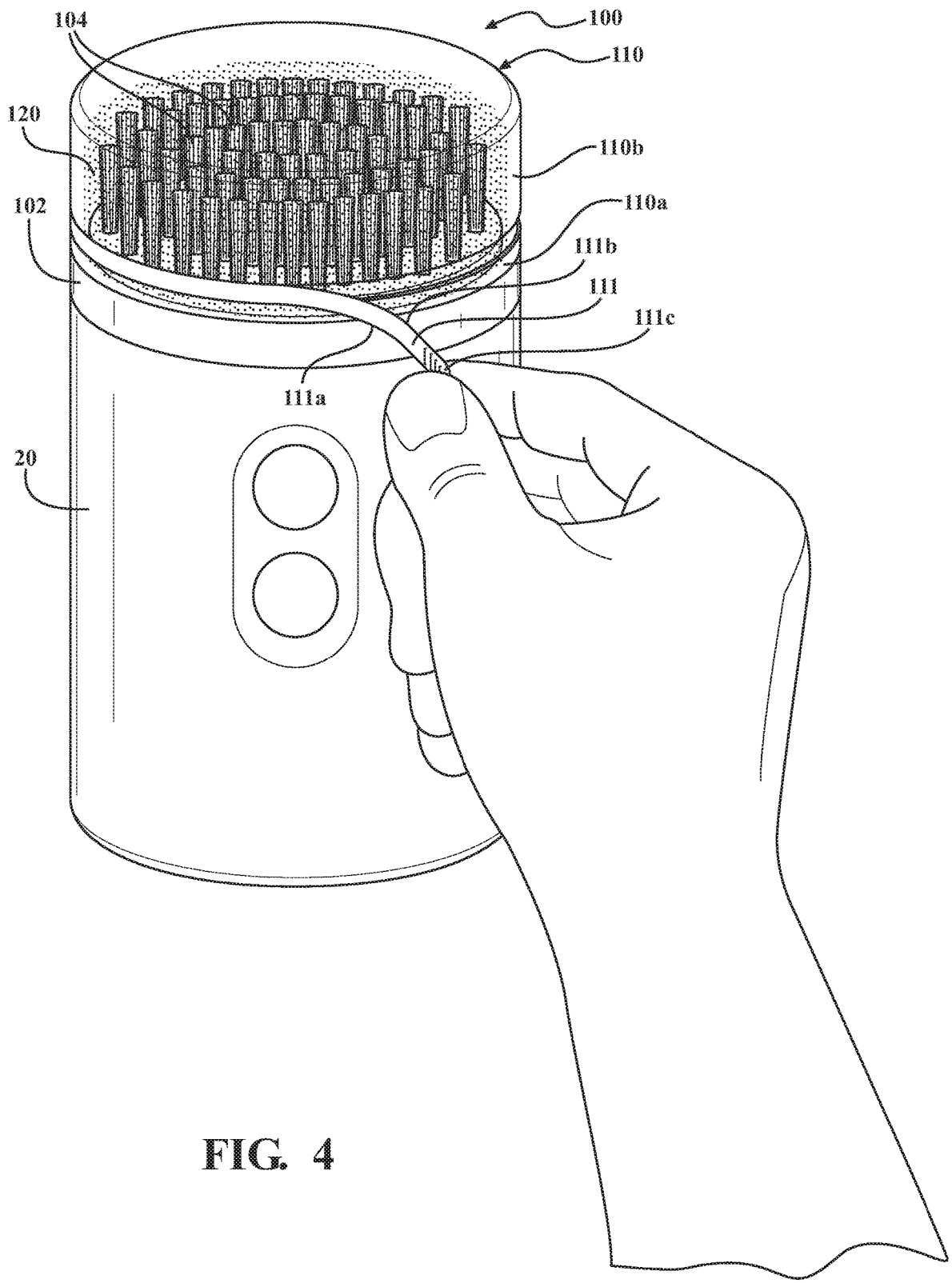
FIG. 4 is similar to FIG. 3 and shows the removable cover of the brush cartridge being removed.
Figure 5:
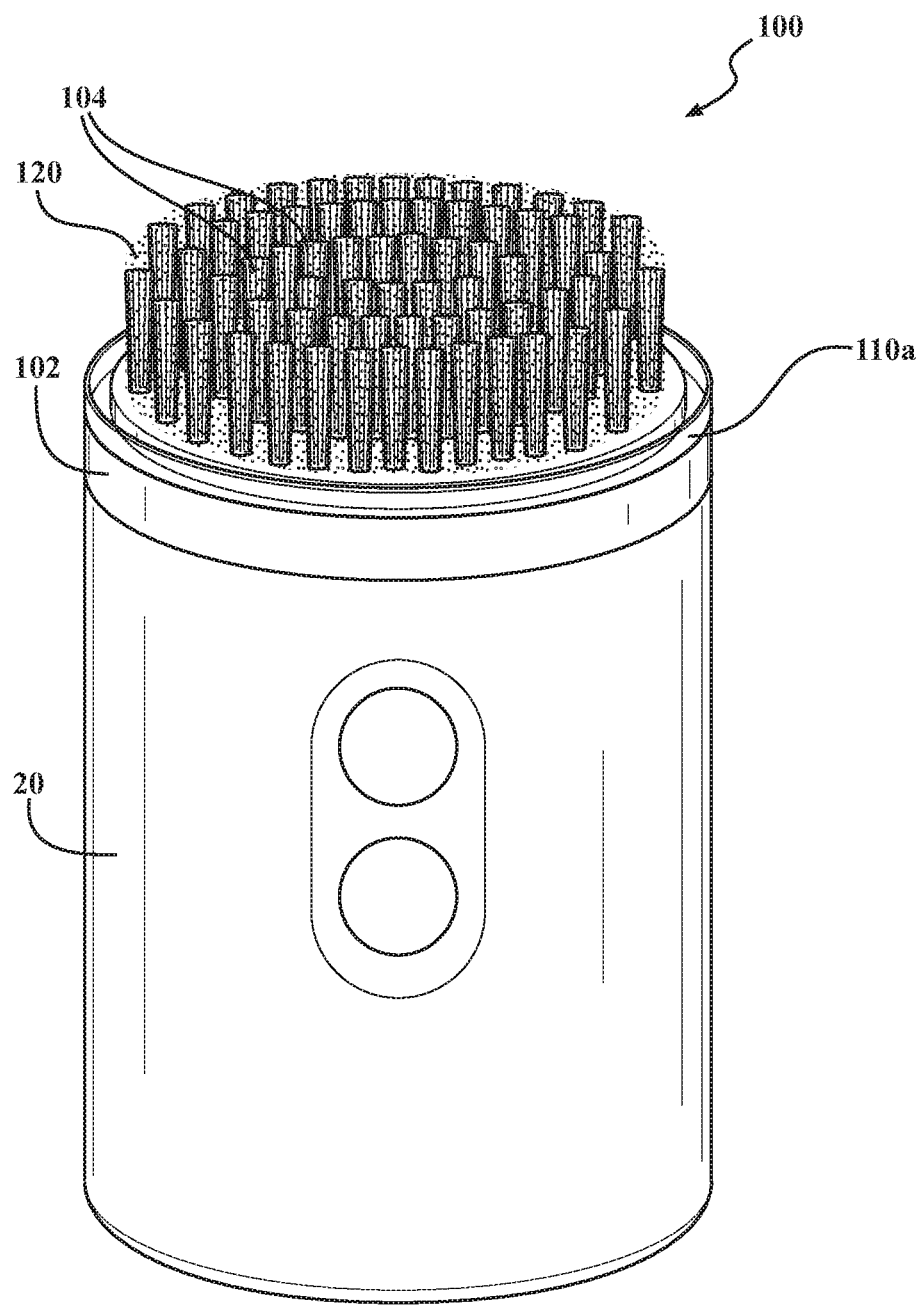
FIG. 5 is similar to FIG. 3 and shows the brush cartridge after the cover has been removed.

Referring in particular to FIGS. 3 and 4, some or all of cover 110 is removable from base 102 in a destructive, one-time, disposable manner; i.e., once removed it is not intended to be replaced over the bristles, in keeping with the sterile and disposable nature of brush cartridge head 100. In the illustrated example, cover 110 has an upper wall 110b connected to lower wall or perimeter edge 110a by a tear-strip 111 of generally known construction. Tear-strip 111 is weakened or pre-stressed at one or both of its edges 111a and 111b without compromising the fluid-tight integrity of the cover, permitting it to be torn away in a circumferential strip from the lower and upper wall sections 110a and 110b of cover 100. When tear-strip 111 is thus removed, upper wall section 110b of the cover can be fully removed from brush cartridge head 100, leaving some or all of the length of bristles 104 exposed above base 102 for skin cleaning operations.

Although tear-strip 111 is shown positioned slightly above a lower perimeter edge or wall 110a of cover 110, it would also be possible to make the tear-strip 111 the border or lowermost edge of cover 110 sealed to base 102, such that when the tear-strip is removed the entire cover 110 is removed from base 102.

While a tear-strip 111 is shown as a means for removing some or all of cover 110 from the base, it would be possible to make some or all of cover 110 removable from base 42 using different materials and/or removal means, potentially including but not limited to removable foil portions, adhesive attachment of the cover to the base, or other known equivalents.

Brush cartridge head 100 also includes a pre-surgical skin cleaning fluid 120 in the surrounding fluid-tight reservoir formed around bristles 104 by base 102 and cover 110. Skin cleaning fluid 120 may vary in composition, depending on the preferences of the surgeon and/or the requirements of a particular procedure or regulatory guidelines, but in a preferred form is a combined solution of known surgical antiseptic and detergents.

The amount of pre-surgical skin cleaning fluid 120 contained in brush cartridge head 100 by cover 110 prior to removing the cover can vary, and may be a separately visible volume as shown schematically in the drawings, or may be a quantity just sufficient to keep bristles 104 moistened until the cover is removed. "Fluid" herein should be understood to include gels and foams, as well as more water-like solutions, and may be in a quantity to submerge the bristles, soak the bristles, or simply keep the bristles moistened, depending on the desired or required level of sterilization and cleansing.

Whatever its consistency or viscosity, fluid 120 should be sterile before applying to the bristles, or at least sterilized after the cover 110 is sealed over the bristles, and cover 110 should additionally be airtight to preserve sterility until opened.

Brush cartridge head 100 (including cover 110) may optionally be partially or entirely enclosed in its own separate disposable sterile wrapper or container (not shown) after being externally sterilized, in order to keep the entire cartridge 100 sterile until needed. Where a brush head cartridge with an independently vibrated portion such as that shown at 42b, 50a in FIG. 1 is used, if the independently vibrated portion is not sealed in fluid-tight fashion between the upper bristle-supporting face 102*a* and the lower side of base 102 or other portion in operative contact with the sonic vibrating mechanism 22, the lower portion of cover 110*a* may be extended around the base of the unit as shown in phantom lines at 110*a*' in FIGS. 2 and 6A to keep the fluid sealed in the reservoir around the bristles; alternately, a separately removable or destructible seal 103 may be used on the lower side of base 102 over the junction of any independently vibrating portion of the base and the remainder of the base to maintain the fluid-tight and sterile integrity of the fluid reservoir established around the bristles 104 by cover 110.

While cover 110 is shown enclosing a volume significantly greater than the volume taken up by bristles 104 on the upper part of the cartridge head, it is possible to size and shape cover 110 to more closely conform to the shape and volume of the bristle array, depending on the desired volume of skin-cleaning fluid 120 contained in the reservoir defined by cover 110 and base 102.

Figure 6A:
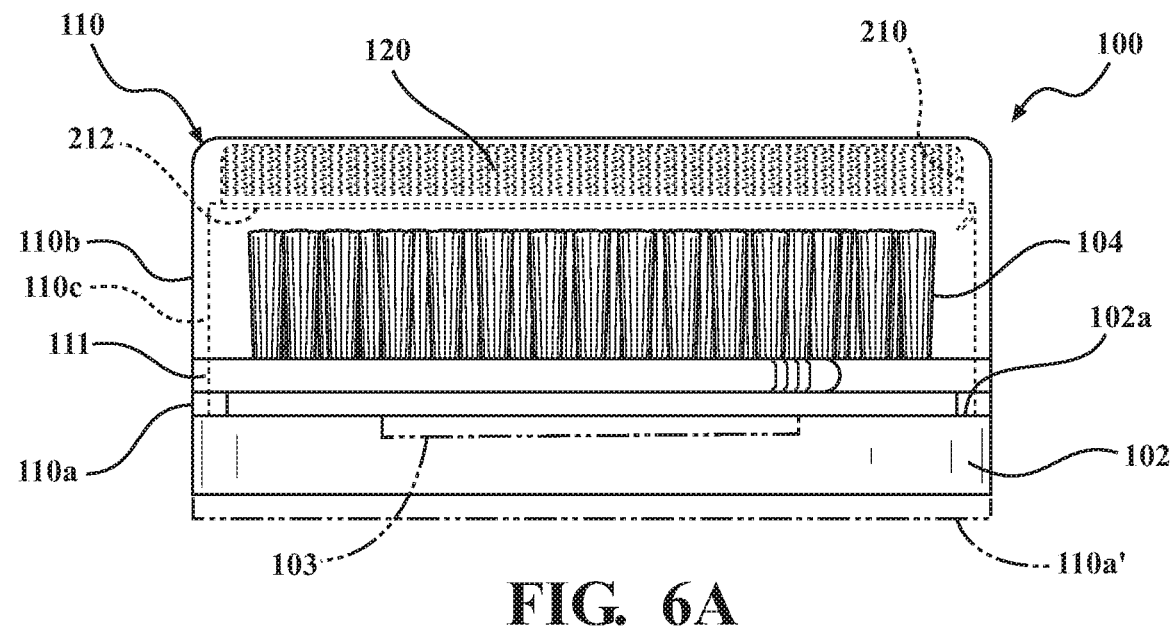
FIG. 6A is similar to FIG. 2, showing a second form of the invention in which the sealed bristle head is divided into two compartments.
Figure 6B:
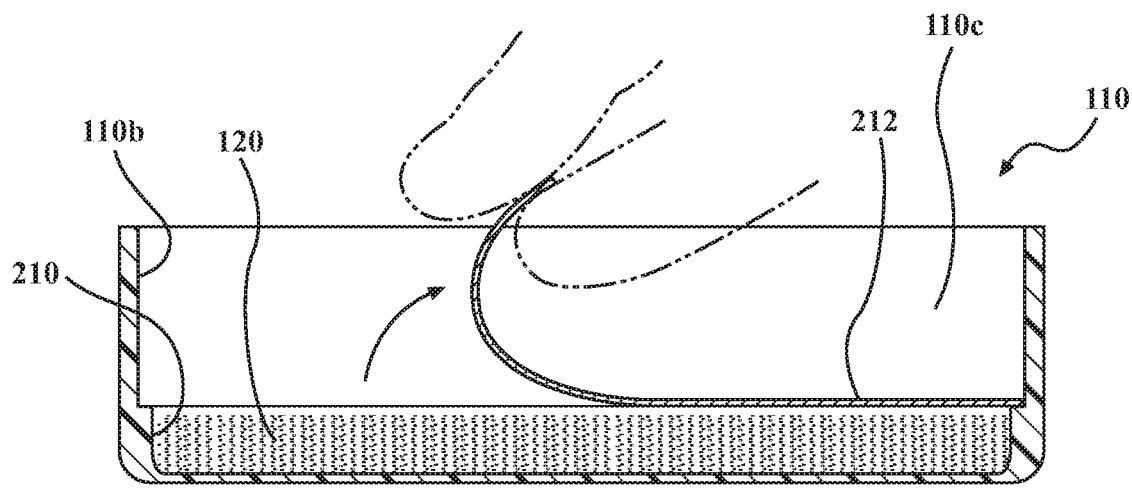
FIG. 6B shows the cover removed from the brush cartridge to access a separate fluid compartment in the cover.

Referring to FIGS. 6A and 6B, brush cartridge head 100 is shown in a modified form, in which cover 110 seals the bristles 104 in a dry, sterile condition in a lower compartment 110*c* defined in a lower part of upper wall portion 110*b*. The skin-cleaning fluid 120 is stored separately in its own sterile, sealed upper fluid compartment 210 located above the lower brush compartment 110*c*. Upper fluid compartment 210 includes its own separate removable seal 212, in the illustrated example a removable metal foil or plastic film seal of known type that can be peeled off to expose fluid 120 after upper cover portion 110*b* of cover 110 has been removed from the brush cartridge 100 as shown in FIG. 6B.

Figure 2:
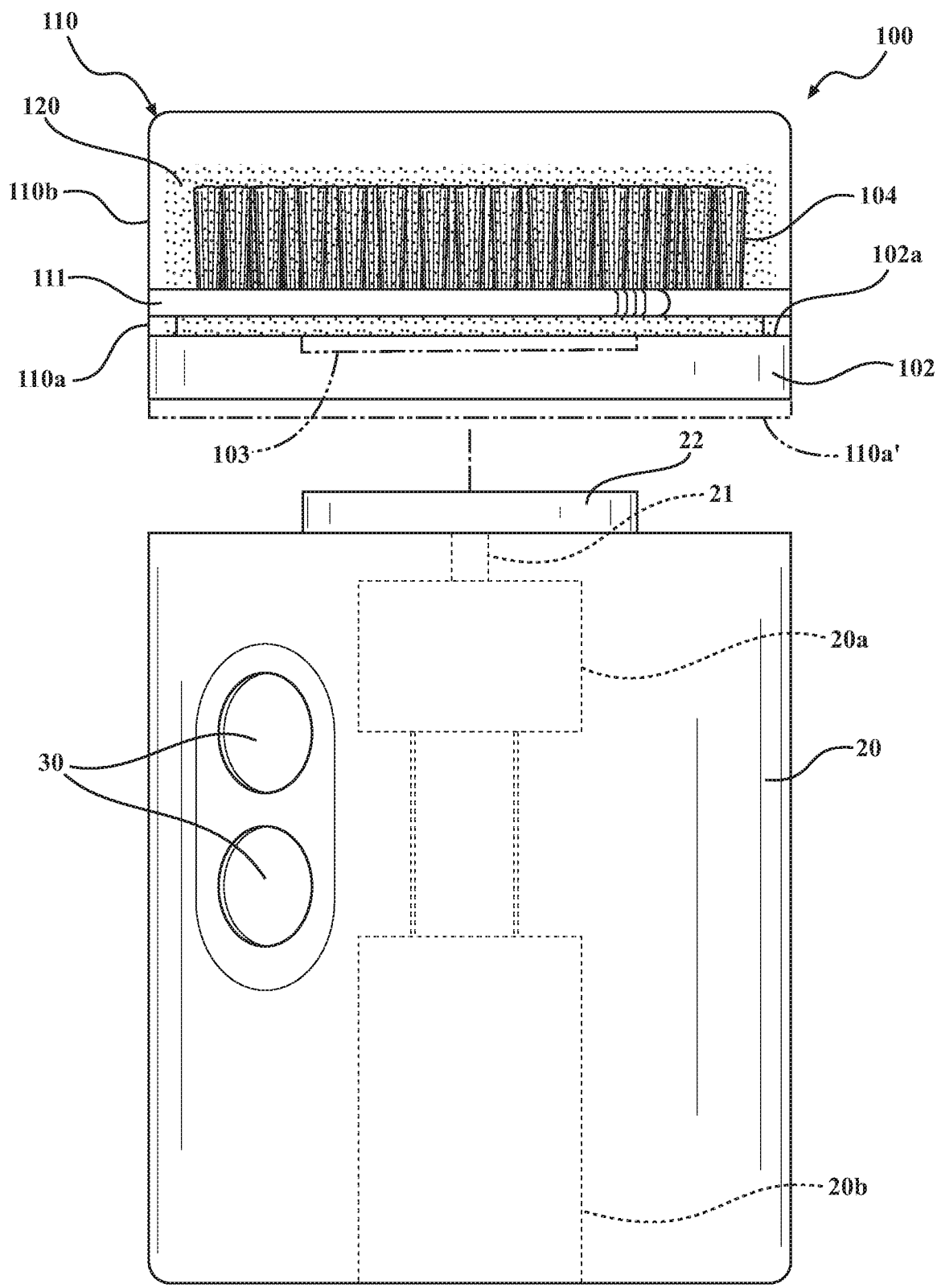
FIG. 2 is a side elevation view of a disposable surgical-prep sonic skin cleaning brush cartridge according to the invention, exploded from a schematically illustrated conventional sonic skin cleaning brush handle of the type shown in FIG. 1.
Figure 7A:
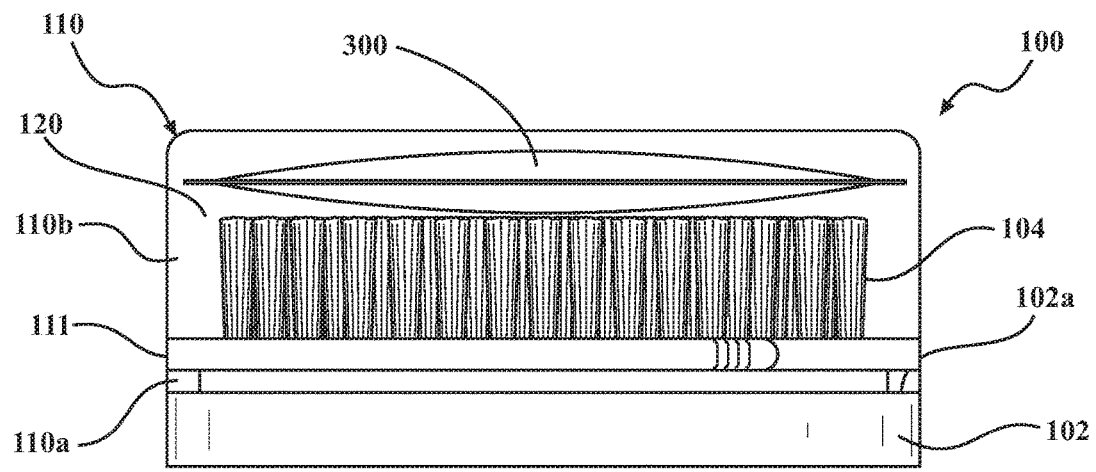
FIG. 7A is similar to FIG. 2, showing a third form of the invention in which the sealed bristle head comprises a single compartment for the brush bristles, and the cleaning fluid is stored in the compartment in its own sealed pouch.
Figure 7B:
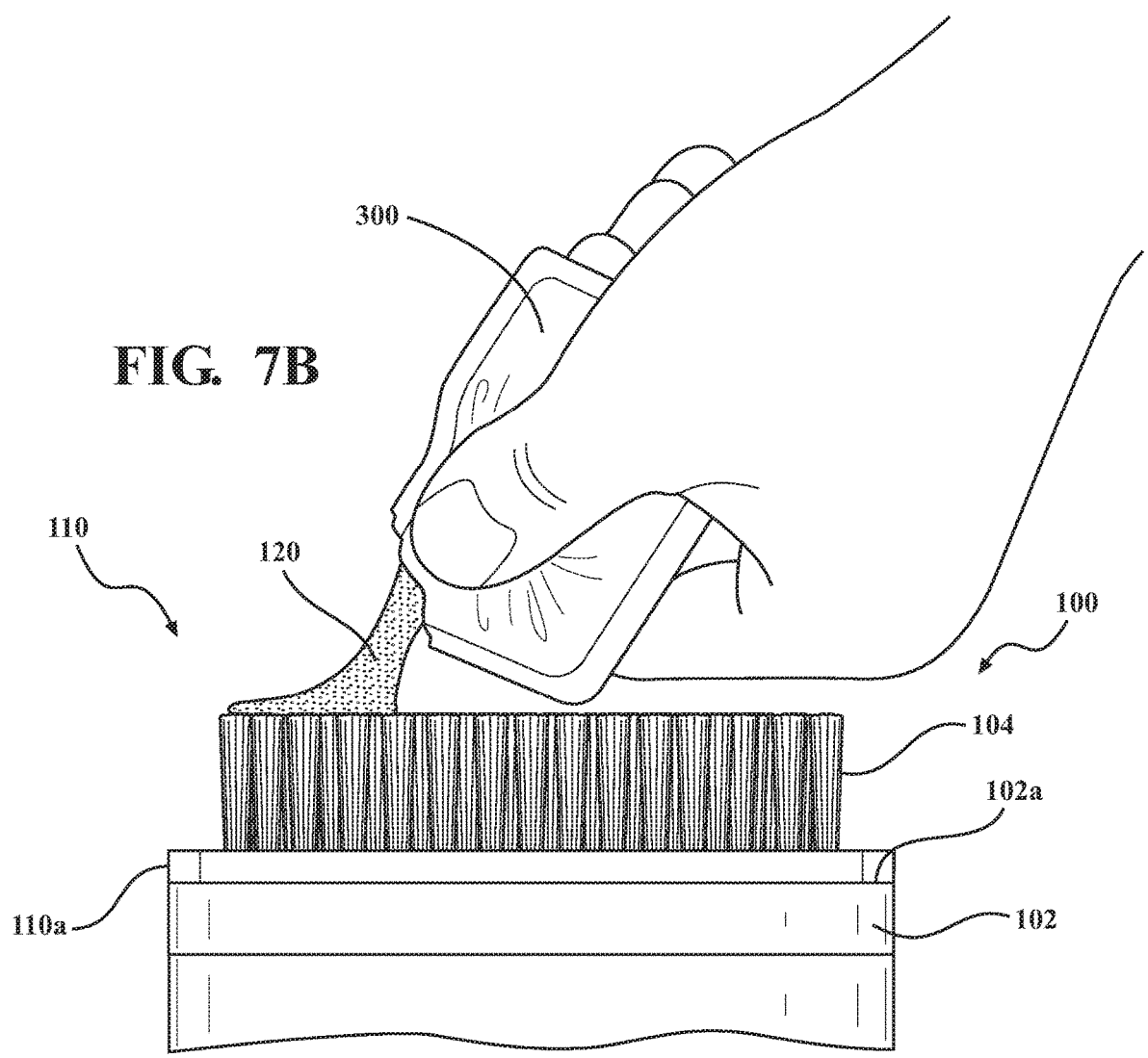
FIG. 7B shows the cover removed from the brush cartridge, and the pouch contents being applied to the bristles.

Referring to FIGS. 7A and 7B, cover 110 contains bristles 104 as in FIG. 2, but the skin cleaning fluid 120 is stored in its own separate, sealed, sterile pouch or other container 300 sealed in the same compartment as the bristles. Once upper cover portion 110*b* of cover 110 is removed from the brush cartridge 100, the contents 120 of pouch 300 can be applied by tearing the pouch open and squeezing or pouring the contents 120 onto the exposed brush bristles 104, as shown in FIG. 7B.

Description of Operation

To use the disposable brush cartridge head 100 of FIGS. 1-5 for a pre-surgical skin preparation, brush cartridge 100 is retrieved from its preferably sterile storage location, any external wrapper or cover is removed, and base 102 is mechanically secured to handle 20. Thereafter, at least the upper portion 110*b* of cover 110 is removed by tearing off tear-strip 111 via gripping tab 111*c*, depositing the removed cover portion and any excess skin-cleaning fluid 120 into a suitable receptacle, and immediately applying the sterile, pre-moistened bristles 104 to the patient's skin at the surgical site and activating the bristles sonically by pressing the suitable control 20*a* on handle 20.

To use the modified brush cartridge head of FIGS. 6A and 6B, cartridge 100 is attached to the handle in the same way as above for FIGS. 1-5. Cover upper portion 110*b* is removed by tearing off tear strip 111 to expose the bristles 104, and then seal 212 is removed from the upper fluid compartment 210 to expose the fluid, which can be applied to the brush head bristles by pouring or by dipping the bristles in the upper fluid compartment.

To use the modified brush cartridge head of FIGS. 7A and 7B, cartridge 100 is attached to the handle in the same way described above for FIGS. 1-5. Cover upper portion 110*b* is removed by tearing off tear strip 111 to expose bristles 104, and then pouch 300 is opened by tearing or cutting to apply the fluid 120 in the pouch to the bristles.

When the skin cleaning procedure is completed, brush cartridge 100 is simply disconnected from handle 20 and discarded in a suitable receptacle.

It will finally be understood that the disclosed embodiments represent presently preferred examples of how to make and use the invention, but are intended to enable rather than limit the invention. Variations and modifications of the illustrated examples in the foregoing written specification and drawings may be possible without departing from the scope of the invention. It should further be understood that to the extent the term "invention" is used in the written specification, it is not to be construed as a limiting term as to number of claimed or disclosed inventions or discoveries or the scope of any such invention or discovery, but as a term which has long been conveniently and widely used to describe new and useful improvements in science and the useful arts. The scope of the invention supported by the above disclosure should accordingly be construed within the scope of what it teaches and suggests to those skilled in the art, and within the scope of any claims that the above disclosure supports in this application or in any other application claiming priority to this application.

The invention claimed is:

1. A disposable sonic brush head cartridge comprising:
 a base comprising a first lower side configured to be removably attached to a sonic skin cleaning brush unit to transmit sonic energy to an array of sonic bristles extending from an oppositely-facing second upper side of the base;
 the array of sonic bristles being sealed with respect to the first lower side of the base with a disposable fluid-tight cover sealed in sterile fluid-tight connection directly to the base and enclosing the array of sonic bristles on the second upper side of the base;
 a reservoir of pre-surgical skin cleaning fluid contained and sealed within the disposable fluid-tight cover on the second upper side of the base; wherein,
 the disposable fluid-tight cover extends beyond and encloses the second upper side of the base around the array of sonic bristles and the reservoir of pre-surgical skin cleaning fluid such that the first lower side of the base may be attached to a sonic skin cleaning brush unit while the array of sonic bristles and the reservoir of pre-surgical skin cleaning fluid remains sealed on the second upper side of the base by the disposable fluid-tight cover; wherein the disposable fluid-tight cover comprises a separately removable seal portion sealed in sterile fluid-tight connection directly to the base and sealing at least a portion of the first lower side of the base.

2. The disposable sonic brush cartridge of claim 1 wherein the separately removable seal portion is configured to be removable from the first lower side of the base to permit attachment of a sonic skin cleaning brush unit to the first lower side of the base.

3. The disposable sonic brush cartridge of claim 2, wherein the disposable fluid-tight cover remains sealed around the array of sonic bristles and the reservoir of pre-surgical skin cleaning fluid on the second upper side of the base when the separately removable seal portion is removed from the first lower side of the base.

\* \* \* \* \*